United States Patent [19]

Choi et al.

[11] Patent Number: 4,612,799

[45] Date of Patent: Sep. 23, 1986

[54] METHOD AND APPARATUS FOR MEASURING VISCOSITY

[75] Inventors: Frank H. Choi, Wappingers Falls; Samuel W. Rein, Poughkeepsie; David L. Alexander, Wappingers Falls, all of N.Y.

[73] Assignee: Texaco Inc., White Plains, N.Y.

[21] Appl. No.: 791,640

[22] Filed: Oct. 25, 1985

[51] Int. Cl.[4] ............................................. G01N 11/12
[52] U.S. Cl. ........................................... 73/54; 73/57; 374/15; 374/23; 374/45; 374/57
[58] Field of Search ................. 374/45, 54, 57, 22, 374/23, 15, 50, 43, 16, 112, 137; 73/54, 57

[56] References Cited

U.S. PATENT DOCUMENTS

| | | | |
|---|---|---|---|
| 1,870,412 | 8/1932 | Kennedy | 73/55 |
| 2,700,228 | 1/1955 | Fainman | 73/57 |
| 3,073,150 | 1/1963 | Fann | 73/54 |
| 3,498,104 | 3/1970 | Kerkvoort et al. | 374/23 |
| 3,798,960 | 3/1974 | Glass | 73/55 |
| 3,977,235 | 8/1976 | Topham | 73/54 |
| 4,048,020 | 9/1977 | Romovacek | 73/57 |
| 4,048,056 | 9/1977 | Romovacek | 73/57 |
| 4,184,364 | 1/1980 | Du Bae | 73/54 |
| 4,466,275 | 8/1984 | Thone | 73/57 |

FOREIGN PATENT DOCUMENTS

| | | | |
|---|---|---|---|
| 1210706 | 10/1970 | United Kingdom | 73/57 |
| 1210804 | 11/1970 | United Kingdom | 73/57 |

*Primary Examiner*—Charles Frankfort
*Assistant Examiner*—Thomas B. Will
*Attorney, Agent, or Firm*—Robert A. Kulason; James J. O'Loughlin

[57] ABSTRACT

A method and apparatus for measuring viscosity of an oil at low temperature and low shear stress. It employs a columnar container of the oil with vertically spaced temperature control devices to apply different cooling histories simultaneously. After the cooling histories have been applied, the viscosity of all the different histories is determined by measuring the instantaneous velocity of a probe moving through the column of oil under a constant force.

12 Claims, 7 Drawing Figures

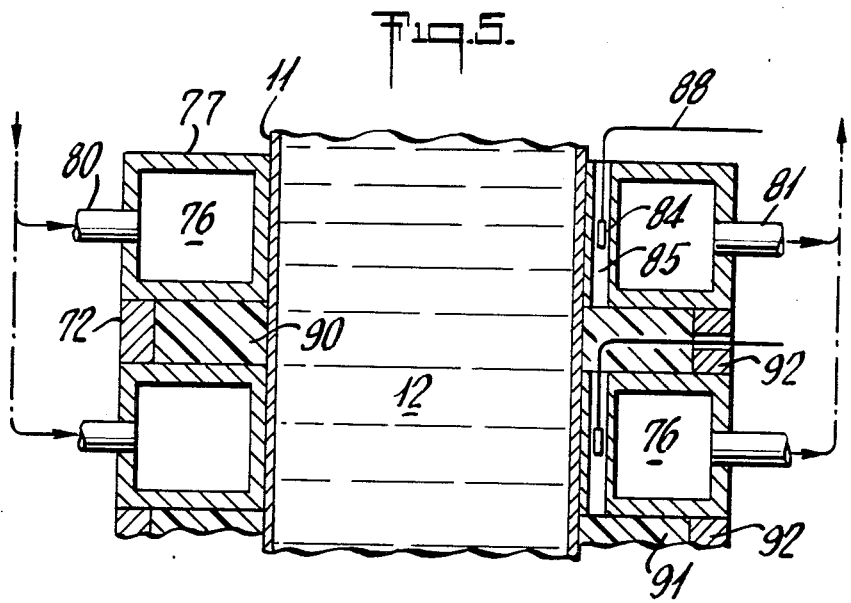
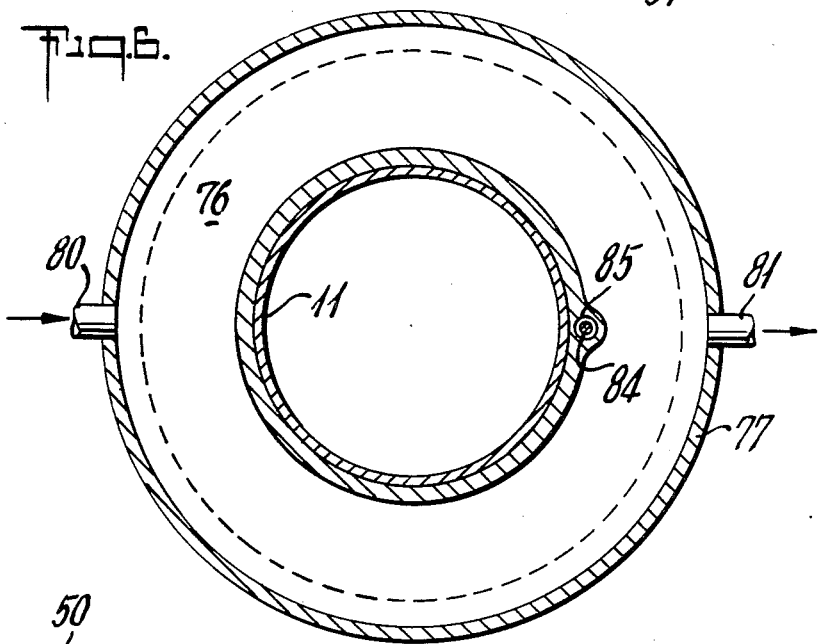
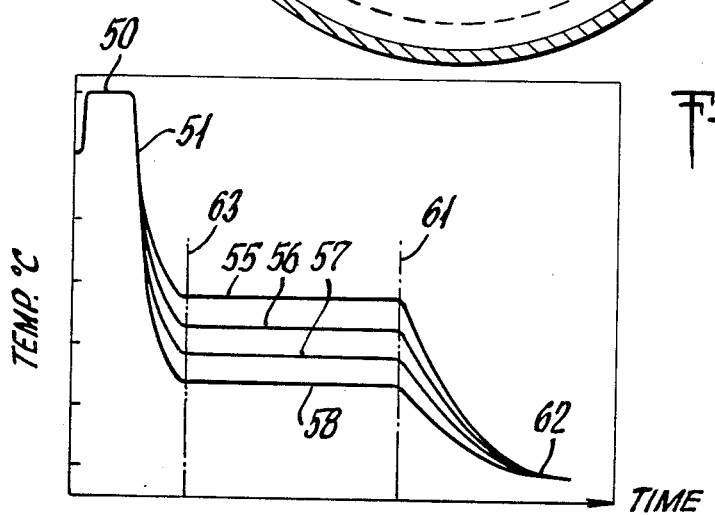

METHOD AND APPARATUS FOR MEASURING VISCOSITY

BACKGROUND OF THE INVENTION

1. Field of the Invention

This invention concerns viscosity measurement in general. More specifically, it relates to a method and system for carrying out a viscosity measurement of lubricating oil to determine low temperature viscosity of engine oils at low shear stress.

2. Description of the Related Art

In testing the viscosity of oils at low temperature and low shear stress, it has been found that viscosity measurements at a chosen low temperature may give different values for different cooling cycles. Sometimes the viscosity may show a strong adverse response to certain types of cooling history. In this connection, engine oil pumpability is an important factor to determine in regard to lubricating oils. Because pumpability may vary with different additives, the testing procedure needs to determine such characteristics for individual oils and/or additives. However, the slow cool conditions involved in pumpability testing require substantial periods of time, e.g. on the order of two days for one cool down cycle. Consequently, testing a given sample for different cooling conditions takes an inordinate amount of time, especially so for running any substantial number of such tests.

There are two U.S. patents known to the applicants which deal with viscosity measurement, namely U.S. Pat. No. 1,870,412 H. T. Kennedy Aug. 9, 1932 and U.S. Pat. No. 3,798,960 J. R. Glass Mar. 26, 1974. However, the Kennedy patent subjects all of a plurality of samples to the same heating and/or cooling conditions so that each sample is subjected to only one cooling condition at a time. Consequently it is not relevant to the applicants invention.

The Glass patent discloses an automatic viscometer system. It makes use of capillary tubes for measuring the viscosity, and a given sample is subjected to unitary temperature conditions during a viscosity measurement. Consequently likewise, it is not relevant to the applicant's invention.

It is an object of this invention to provide a method and system for concurrently applying a plurality of cooling conditions or cycles to separate portions of a single sample to be tested. That is followed by measuring the viscosity of the whole sample including all of the cycles.

Another object of the invention is to provide for running a test cycle that includes a plurality of different test cooling conditions simultaneously. It ends with viscosity tests for all of said plurality of cooling cycles at relatively the same time.

SUMMARY OF THE INVENTION

Briefly, the invention concerns a method of measuring viscosity of a lubricating oil at low temperature and low shear stress, after a plurality of different cooling histories are applied concurrently. It comprises subjecting an upstanding column of said lubricating oil to a predetermined high temperature throughout the length thereof, and cooling said column at a plurality of vertically spaced locations with different cooling histories. It also comprises measuring the viscosity of said column over all of said vertically spaced locations at a predetermined low temperature, following the application of said cooling histories.

Again briefly, the invention concerns a method of measuring viscosity of a lubricating oil at low temperature and low shear stress after a plurality of different cooling histories are applied concurrently to the same sample. It comprises (1) subjecting a vertical column of said oil sample to a predetermined high temperature throughout the length thereof, and (2) cooling said sample at a plurality of vertically spaced locations with separately controlled cooling rates to provide said different cooling histories. The said cooling histories comprise (a) rapid cooling of all said locations down to a soaking temperature for each location, the highest of said soaking temperatures being at the top of said locations. The cooling histories also comprise (b) holding said soaking temperatures substantially constant for a predetermined length of time, and (c) cooling said locations after said soaking temperatures, at a predetermined rate of cooling to a predetermined low temperature. The method also comprises (3) measuring the viscosity of all said vertical column, said measuring comprising (a) driving a probe downwards through said locations at a constant driving force, and (b) measuring the velocity of travel of said probe whereby said viscosities may be determined.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 5 is an enlarged longitudinal cross-sectional detail, showing two of the individual cooling jacket structures employed;

FIG. 6 is a horizontal cross-sectional view of the elements shown in FIG. 5; and FIG. 7 is a graph illustrating a plurality of cooling cycles which are carried out simultaneously in connection with the invention.

DESCRIPTION OF THE PREFERRED EMBODIMENTS

There have been numerous engine failures that were found to have been caused by low temperature pumpability deficiencies in the engine oil employed. Consequently, it has been an important area for investigation to determine the effects of various cooling rates, or cooling histories of lubricating oils that might adversely effect the pumpability at very low temperatures.

The foregoing investigation was developed into a particular cooling procedure, and the one most often used encompassed a two-day cool down test. After the test oil sample was raised to 80° C. and held at that temperature for a predetermined time, it was rapidly cooled to −8° C. and then slowly cooled at a rate of 0.33° C. per hour which took about 40 hours. Thereafter, the test oil was cooled to some appropriate test temperature (depending upon the viscosity grade of the oil) at a rate of 2.5° C. per hour.

The cooling procedure according to the foregoing was carried out on an individual sample of the oil and it will be observed that the time required was extremely long. However, it has been discovered that by employing a procedure according to this invention, a number of different cooling histories may be applied to the same sample of oil at the same time. Thereafter, the viscosity measurement may be carried out for all of the plural cooling histories applied. Consequently, only the time required for a single one of the cool down histories is used to determine a plurality of different cool down histories, for evaluation thereof.

Figure 1:
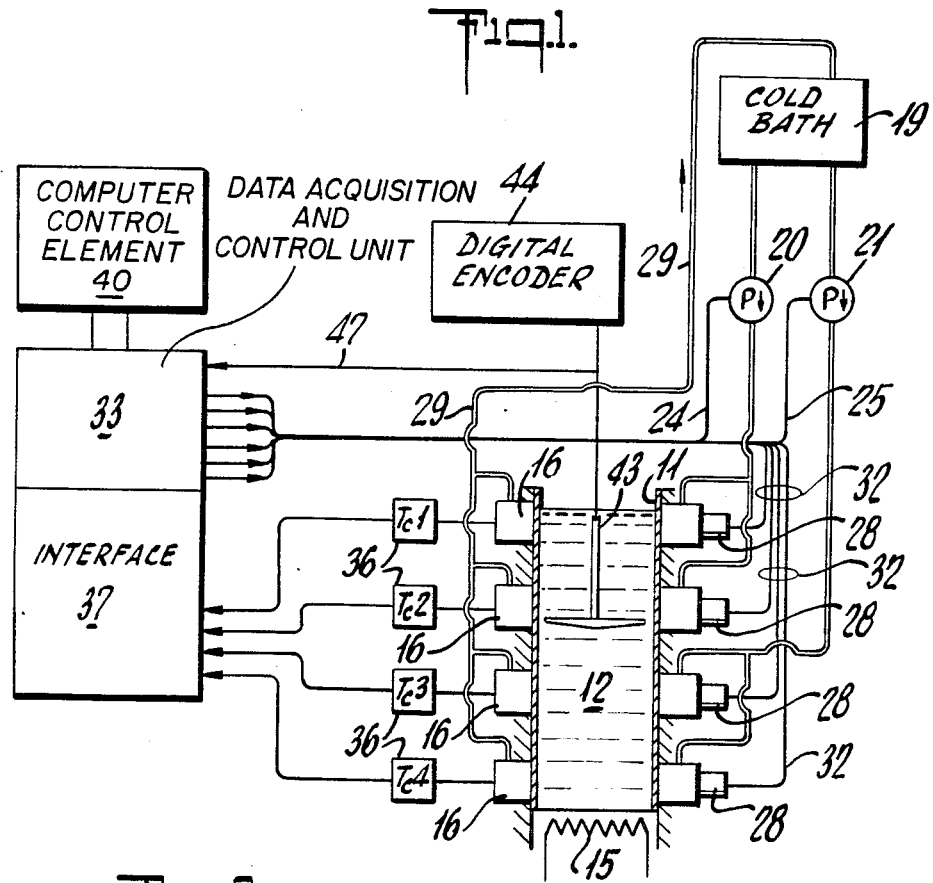
FIG. 1 is a diagrammatic illustration showing a complete system for carrying out a method according to the invention.

FIG. 1 is a schematic illustration showing a system for carrying out the invention. There is a cylindrical container 11 that has heat conductive walls. It holds a column of oil 12 that is to be tested. There is a schematically indicated heater 15 for heating the sample to a beginning high temperature. It may be noted that although the heater 15 is shown in the schematic as being located at the bottom of the oil column 12, it is preferably a horizontally situated cartridge (not shown) in a vertical heater plate (not shown) adjacent to the column 12. Also, FIG. 1 shows four cooling jackets 16 that are schematically indicated. These jackets 16 surround the container 11 and are spaced apart vertically from one another so that during the cooling cycles, layers of the oil 12 (opposite each of the cooling jackets 16) may have different cool down histories applied at the same time.

In order to accomplish the foregoing, there is a cold bath supply 19 containing a coolant at −40° C. One coolant fluid with the ability to hold that temperature is methanol, although of course other fluids might be employed. There are two circulating pumps 20 and 21 that are connected to the cold bath 19. These pumps are controlled for turning them on and off by electrical circuit connections 24 and 25 respectively. Each pump, 20 and 21, has its output connected to two of the jackets 16 via two of a corresponding number of valves 28. Return flow of the coolant from the other side of each jacket 16 goes to a common return line 29 that leads back into the cold bath 19.

The valves 28 are solenoid actuated and there are electrical circuit connections 32 that go to a data acquisition and control unit 33, along with the circuit connections 24 and 25 which control the pumps 20 and 21. There are temperature control elements 36 which are designated Tc1-Tc4. These incorporate temperature measuring elements (not shown in FIG. 1) which provide signals by translating thermistor resistances into temperature signals that are connected to an interface 37. In interface 37, signals from the temperature control elements 36 are applied to the control unit 33.

Data acquisition and control Unit 33 is an appropriate computer such as one manufactured by Hewlett Packard designated HP-3421A. It has the ability to coordinate the real time temperature measurements and the controls of the solenoid valves 28, along with the pumps 20 and 21 in order to apply individual cool down cycles to each of the locations of jackets 16. These locations are spaced along the column of oil 12.

The data acquisition and control unit 33 is in turn controlled by a computer control element 40 which may be a personal computer such as one manufactured by Hewlett Packard and designated HP-86B. The control element 40 is programmed for causing the individual solenoid valves 28 to be manipulated so as to control the circulation of coolant from the supply 19 in accordance with the temperature at each jacket 16.

When the temperatures at the locations of the jackets 16 are being kept at different readings, i.e. during temperature soaking times, the highest temperature is located at the uppermost jacket 16. This maintains a continuous gradient of temperatures from one jacket 16 level to the next.

The circulation controls which are being applied to the coolant that is supplied from the cold bath 19, include control of energization of the pumps 20 and 21 whenever either or both of the valves 28 (to which the respective pump is connected) is or are opened for permitting circulation of coolant. It will be understood that these controls are carried out in accordance with software programs that are written to execute the predetermined cool down histories at the separate locations of the jackets 16.

In order to measure the individual viscosities of the oil sample 12 at the separate levels of each of the jackets 16 after all of the individual test cycles have been applied, there is a probe 43 that is connected with a digital encoder 44. The instantaneous velocity of the probe 43 is measured by having an electrical circuit connection 47 that goes to the unit 33. As will appear in more detail below, the probe 43 is provided with a constant driving force to move it through the column of oil 12. Therefore, the instantaneous velocity is measured by using the output of the encoder 44 which may be calibrated in terms of viscosity of the oil in column 12.

A preferred method according to this invention may be described in connection with the schematic diagram of FIG. 1. It will be appreciated that other and/or different means might be employed in carrying out the invention. The method is one for measuring viscosity of a lubricating oil at low temperature and low shear stress, after a plurality of different cooling histories have been applied concurrently to the same sample. Thus, as indicated in FIG. 1, there is a sample of oil 12 to which plural cooling histories are applied substantially at the same time. This is done by means of the cooling jackets 16.

The method includes a step of subjecting a vertical column of the oil, e.g., column 12, to a predetermined high temperature throughout the length thereof. This of course may be carried out by applying heat from the heater 15 to the entire column of oil 12. Application of heat is continued long enough to heat the entire column to a predetermined temperature, such as a high temperature level 50 illustrated on the graph of FIG. 7. As mentioned above, the high temperature that is employed with a cooling procedure for testing low temperature pumpability, is usually 80° C. That high temperature is continued for a predetermined length of time, such as the above indicated two-hour period.

A next step is that of cooling the oil sample 12 at all of the vertically spaced locations, i.e. opposite each of the cooling jackets 16. While the rates of cooling at the plural locations are separately controlled (so as to create a gradient of cooling histories) all of the cooling histories begin with the same rapid cooling. Such rapid cooling continues until the beginning of each of the soaking temperatures. Such soaking temperatures are different for each jacket location. This cooling is indicated by a steep temperature decrease 51 on the FIG. 7 graph. It will be appreciated that all of these first portion of the individual cooling histories, 50 and 51 in FIG. 7, are the same and are carried out together by the controls described above. Those controls activate both pumps 20 and 21 as needed and control the valves 28 individually to be open or closed for controlling circulation of the coolant from cold bath 19.

When the temperatures at locations opposite the control jackets 16 reach the predetermined soak temperatures for those locations, (time 63 in FIG. 7), the temperature control elements 36 (Tc1-Tc4) close their respective solenoid valves 28 to begin regulation of the cooling rate to maintain the temperature substantially constant at each of these locations. During the ensuing soak period, a constant temperature gradient is maintained in column 12, with the highest temperature at the top and the lowest temperature at the bottom. Intermediate points in column 12 will have intermediate temperatures approximately proportional to their vertical distance from top or bottom. The specific locations opposite the control jackets 16 will be at temperatures corresponding to the jacket temperatures, indicated by horizontal lines 55-58 in FIG. 7. The oil column 12 is soaked at this temperature gradient for a predetermined time, from 63 to 61 in FIG. 7. During this time, the temperature gradient is maintained by close control of the coolant flow. That control is carried out by controlling the solenoid valves along with the pumps so as to circulate the coolant as necessary. The result creates a gradient of individual cooling histories controlled at separate layers of the oil in the column 12, all at the same time. The soaking time periods for all of the range of temperatures are maintained for a very substantial length of time as indicated above in the general description of a cooling cycle test.

At the end of the foregoing soaking periods, which take about 18 hours, the last part of the cooling histories that are applied to the plural layers of the oil column 12 involves cooling them all at a predetermined rate to an appropriate temperature for making viscosity measurements. The appropriate temperatures for SAE grades 5W, 10W and 15W are $-30°$ C., $-25°$ C. and $-20°$ C. respectively. This final portion of the plural cooling histories is illustrated in the FIG. 7 graph at the right hand side of a broken line 61. This illustrates the fact that all of the range of histories end at a predetermined low temperature which is indicated at a location 62.

A final step concerns measuring the viscosity of all the locations that had the separate cooling histories applied to them. To do that it is necessary to drive the probe 43 down through the oil column 12 with a constant driving force. Also, the instantaneous velocity of the probe is measured. Such velocity measurement is carried out accurately by employing the digital encoder 44 (illustrated in FIG. 1) and by feeding the information to the computer unit 33 via an electrical circuit indicated by the line 47. The viscosity is determined from the fact that the velocity is a function of the viscosity. Then, as soon as the last of the locations has been traversed the results will provide information on all of the whole range of plural cooling histories.

The four constant temperature lines, 55-58 in FIG. 7, represent the four locations in the oil column 12 at which the temperature is controlled. The column 12 is actually subjected to a continuum of parallel cooling histories between the locations represented by lines 55-58. To the extent that the oil being tested is responsive to cooling history, viscosity will vary continuously along the column. And, at each height in the column, the viscosity will correspond to the cooling history for that location. Thus, as the probe 43 moves down through the oil column 12, it senses the viscosity corresponding to its location along the column.

Figure 2:
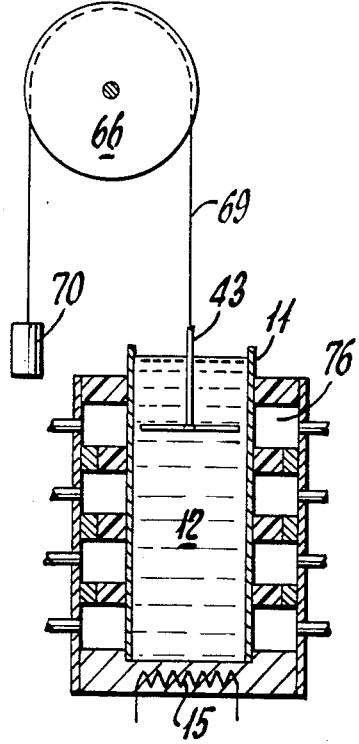
FIG. 2 is a schematic illustration of a portion of the FIG. 1 system, showing a pulley for supporting the probe in the column of oil being tested.

FIG. 2 illustrates in greater detail the structure that is schematically indicated in FIG. 1 relating to the container 11 and the cooling jackets 16. Thus, the container 11 as illustrated in FIG. 2, contains the column of oil 12. The probe 43 is suspended in the column of oil 12 by a pulley 66 in order to provide sufficient offset for a counter weight 70 attached to the other end of a line 69.

The constant driving force that is mentioned above and which is applied to the probe 43, might be accomplished by different arrangements. However, as indicated in FIG. 2 it is carried out by having the pulley 66 mounted so that the probe 43 is suspended from the flexible line 69 with the counter weight 70 at the other end of the line 69. The counter weight 70 is chosen so as to leave a desired amount of positive net weight of the probe 43. It is that net weight which applies the constant driving force.

Figure 3:
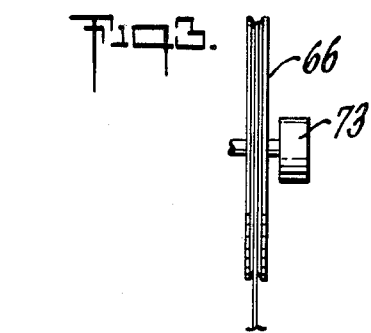
FIG. 3 is an end elevation, somewhat enlarged, illustrating the pulley shown in FIG. 2 and including a digital encoder for measuring the velocity of the probe.

FIG. 3 illustrates an end view of the pulley 66 which shows an encoding element 73 that is driven by the shaft of pulley 66. It will be appreciated that element 73 might take different forms as part of the encoder 44 that is indicated in FIG. 1.

Figure 4:
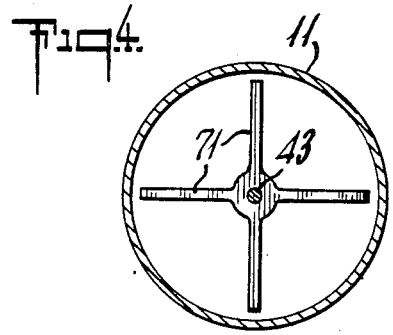
FIG. 4 is a cross-sectional view showing the configuration of a typical probe being used for the viscosity measurement.

FIG. 4 illustrates the lower end of the probe 43 which has a simple cross-armed shape 71. However, it will be appreciated that there might be many various and different shapes employed (not shown) depending upon various considerations. The only limitation for the probe shapes is that the vertical dimension must be small, i.e., the probe needs to be thin, in order that the viscosity measurement is sufficiently confined vertically in the oil column 12. This is necessary in order to accurately measure viscosity at each of the locations where the different cooling histories were applied.

FIGS. 5 and 6 show structure of two of the jackets 16 that are schematically indicated in FIG. 1. At each jacket location there is an annular passage 76 formed inside of a metallic jacket 77 that has a rectangular shape in cross section. Each passage 76 has an inlet pipe 80 connected through the outside wall at one side, and an outlet pipe 81 connected through the outside wall at the other side diagonally across from the inlet pipe 80. These pipes are for circulating the coolant into and out of the annular passage 76. In order to carry out the temperature control at each location, there is a thermistor 84 located in a well 85 drilled into the inner wall of the jacket 77. Control signals from the thermistor 84 are carried via an electrical circuit connection 88 so that desired control signals may be used in controlling the cooling process at each of the locations.

It may be noted that between the metallic jackets 77 there are insulating material filled spaces 91 which surround the container 11. This separates the layers of the column of oil 12 that have the individual cooling histories applied to them. There are also metallic spacers 92 for separating the hollow jackets 77 and for containing the insulation in the spaces 91. It will be appreciated that the different temperatures maintained at the separate layers of the column of oil 12 during the soaking times, will have a gradient of temperature change from one layer to the next but without any thermal current mixing between layers. That is because the higher temperatures are above the lower temperatures throughout the column 12.

It may be noted that while the foregoing description with illustrations indicates a single test specimen of oil being tested, it is contemplated that a greater number of samples to be tested could be done coextensively. That would be done by locating a plurality (not shown) of columns of sample oil at various locations radially situated around a central point. In that manner each might have its viscosity tests run successively after all of the plurality of different oil samples had the plural cooling histories of each run simultaneously. Each individual sample would have its plural histories applied, in substantially the same manner and at the same time as was the case with the one oil sample with plural histories as described in the foregoing. In that manner a single probe could be employed for all of the plural oil samples in sequence, after the plural cooling histories for each sample had been run at the same time. This is so because the length of time for carrying out the viscosity measurements is not great and could be done on each different oil sample, one after the other following the multiple cooling history applications at the different levels for each oil sample.

It will be appreciated that the particular temperature cycle illustrated and described in the foregoing should not be considered limiting since other cooling cycles could be performed by the type of equipment shown.

While particular embodiments according to this invention have been described above in considerable detail in accordance with the applicable statutes, this is not to be taken as in any way limiting the invention but merely as being descriptive thereof.

We claim:

1. Method of measuring viscosity of a lubricating oil at low temperature and low shear stress after a plurality of different cooling histories have been applied concurrently, comprising
   subjecting an upstanding column of said lubricating oil to a predetermined high temperature throughout the length thereof,
   cooling said column of oil at a plurality of vertically spaced locations with different cooling histories, and
   measuring the viscosity of said column of oil over all of said vertically spaced locations at a predetermined low temperature following the application of said cooling histories.

2. Method of measuring viscosity according to claim 1, wherein
   said cooling histories comprise a rapid cooling from said high temperature down to a predetermined soaking temperature for each location, the highest of said soaking temperatures being at the top of said column of oil, and
   cooling all of said locations from said soaking temperatures down to said predetermined low temperature.

3. Method of measuring viscosity according to claim 2, wherein
   said measuring the viscosity comprises
   driving a viscosity-measuring probe downward through said column of oil 0:1 at a predetermined constant driving force, and
   measuring the velocity of travel of said probe whereby said viscosity may be determined.

4. Method of measuring viscosity of a lubricating oil sample at low temperature and low shear stress after a plurality of different cooling histories have been applied concurrently to the same sample, comprising
   (1) subjecting a vertical column of said oil sample to a predetermined high temperature throughout the length thereof,
   (2) cooling said sample at a plurality of vertically spaced locations with separately controlled cooling rates to provide said different cooling histories, said cooling histories comprising
      (a) rapid cooling of all said locations down to a soaking temperature for each location, the highest of said soaking temperatures being at the top of said locations,
      (b) holding said soaking temperatures substantially constant for a predetermined length of time, and
      (c) cooling said locations after said soaking temperatures at a predetermined rate of cooling to a predetermined low temperature, and
   (3) measuring the viscosity of all of said vertical column of oil, said measuring comprising
      (a) driving a probe downward through said locations at a constant driving force, and
      (b) measuring the velocity of travel of said probe through each location whereby said viscosities may be determined.

5. System for testing a sample of fluid for determining viscosity after a plurality of cooling histories have been applied to said sample concurrently, comprising
   means for containing a column of said fluid sample,
   means for applying said cooling histories to said column of fluid at spaced locations there along concurrently, and
   means for measuring the viscosity of said column of fluid over said spaced locations after said cooling histories have been applied whereby the viscosity of said sample may be determined for each of said cooling histories concurrently.

6. System according to claim 5, wherein
   said means for applying said cooling histories, comprises
   heat transfer means associated with said spaced locations, and
   means for controlling said heat transfer means to apply each of said cooling histories separately.

7. System according to claim 6 wherein
   said means for containing a column of fluid sample, comprises
   an upstanding cylindrical container having heat conductive walls.

8. System according to claim 7, wherein
   said means for measuring the viscosity, comprises
   a probe for moving through said column of fluid sample,
   means for applying a constant force to said probe, and
   means for measuring the velocity of said probe whereby said viscosity may be determined.

9. System for testing a sample of fluid for determining viscosity after a plurality of cooling histories have been applied to said sample concurrently, comprising
   an upstanding cylindrical container for holding a column of said fluid sample and having heat conductive walls,
   heat transfer means associated with said cylindrical container at spaced locations there-along, means for controlling said heat transfer means to apply one of said cooling histories at each of said spaced locations, a probe for moving through said column of fluid sample, means for applying a constant force to said probe, and means for measuring the velocity of said probe throughout said column whereby said viscosity may be determined.

10. In combination, a vertically oriented columnar container for holding a sample of lubricating oil to be tested for low temperature viscosity under controlled cooling conditions, a plurality of vertically spaced means for controlling the temperature of said sample at vertically spaced locations along said container, a viscosity probe adapted for longitudinal movement through said sample inside said container, means for applying a constant driving force to said probe, and means for measuring the velocity of said probe through said sample whereby the viscosity at said vertically spaced locations may be determined.

11. The invention according to claim 10, wherein said vertically spaced means, comprises jackets surrounding said container, a coolant for circulating through said jackets, and means for controlling circulation of said coolant through each of said jackets.

12. The invention according to claim 11, wherein said means for controlling circulation, comprises pump means, and valve means for each of said jackets.

* * * * *